US011512031B2

(12) United States Patent
Hamilton et al.

(10) Patent No.: US 11,512,031 B2
(45) Date of Patent: Nov. 29, 2022

(54) METHODS FOR LIMITING WATER IN RECYCLED SOLVENT DURING LINEAR ALPHA OLEFIN SYNTHESES

(71) Applicant: ExxonMobil Chemical Patents Inc., Baytown, TX (US)

(72) Inventors: Paul Hamilton, Hampshire (GB); Terrance C. Osby, Spring, TX (US); Brian W. Heins, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/297,392

(22) PCT Filed: Nov. 14, 2019

(86) PCT No.: PCT/EP2019/081272
§ 371 (c)(1),
(2) Date: May 26, 2021

(87) PCT Pub. No.: WO2020/114743
PCT Pub. Date: Jun. 11, 2020

(65) Prior Publication Data
US 2022/0002215 A1    Jan. 6, 2022

Related U.S. Application Data

(60) Provisional application No. 62/774,955, filed on Dec. 4, 2018.

(30) Foreign Application Priority Data

Feb. 19, 2019    (EP) ..................................... 19158086

(51) Int. Cl.
*C07C 2/30*    (2006.01)
*B01D 3/14*    (2006.01)
(Continued)

(52) U.S. Cl.
CPC ................ *C07C 2/30* (2013.01); *B01D 3/141* (2013.01); *B01D 3/143* (2013.01); *B01J 31/223* (2013.01);
(Continued)

(58) Field of Classification Search
CPC .. C07C 2/30; C07C 7/005; C07C 7/04; C07C 2531/22; B01D 3/141; B01D 3/143; B01J 31/223
See application file for complete search history.

(56) References Cited

U.S. PATENT DOCUMENTS

2007/0185361 A1*   8/2007   Buchanan ................. C07C 2/32
                                                       585/521
2010/0217058 A1*   8/2010   Fritz ......................... C07C 2/08
                                                       585/520
2018/0327332 A1*   11/2018   Sogo ......................... C07C 2/30

* cited by examiner

*Primary Examiner* — Ali Z Fadhel
(74) *Attorney, Agent, or Firm* — ExxonMobil Chemical Patents Inc.

(57) ABSTRACT

Linear alpha olefins (LAOS) may be formed by oligomerization of ethylene in the presence of a Ziegler-type catalyst. The presence of trace water during oligomerization can result in unwanted formation of insoluble higher oligomers or polymer. Methods for limiting the presence of water during ethylene oligomerization reactions may include separating residual ethylene and 1-butene from an LAO product stream to form a higher LAO-enriched stream comprising $C_{6+}$ LAOs, separating 1-hexene as an overhead stream from the higher-LAO enriched stream using a first distillation column, obtaining separated solvent as a side stream from the first distillation column or as a side stream from a first of one or more downstream distillation columns, and returning the separated solvent to a reactor in a recycled solvent stream. The recycled solvent stream passes through one or more driers before returning to the reactor.

22 Claims, 3 Drawing Sheets

(51) Int. Cl.
*B01J 31/22* (2006.01)
*C07C 7/00* (2006.01)
*C07C 7/04* (2006.01)

(52) U.S. Cl.
CPC ................ *C07C 7/005* (2013.01); *C07C 7/04* (2013.01); *C07C 2531/22* (2013.01)

METHODS FOR LIMITING WATER IN RECYCLED SOLVENT DURING LINEAR ALPHA OLEFIN SYNTHESES

CROSS-REFERENCE TO RELATED APPLICATIONS

This application is a National Phase Application claiming priority to PCT Application Serial No. PCT/EP2019/081272 filed Nov. 14, 2019, which claims the benefit of U.S. Provisional Patent Application 62/774,955, filed on 4 Dec. 2018, entitled METHODS FOR LIMITING WATER IN RECYCLED SOLVENT DURING LINEAR ALPHA OLEFIN SYNTHESES, and European Patent Application Number 19158086.9, filed on 19 Feb. 2019, entitled METHODS FOR LIMITING WATER IN RECYCLED SOLVENT DURING LINEAR ALPHA OLEFIN SYNTHESES, the disclosures of which are incorporated by reference herein in their entireties.

FIELD

The present disclosure relates to linear alpha olefin (LAO) syntheses.

BACKGROUND

Linear alpha olefins (LAOs), which also may be referred to as linear alpha alkenes, linear terminal olefins, linear terminal alkenes, or normal alpha olefins are a commercially valuable class of chemical compounds. Polymerization is the primary market for LAOS, in which they are most frequently used as a co-monomer during copolymerization of ethylene. Another significant market for LAOs is as a precursor for linear aldehydes and carboxylic acids formed through oxidation, as a precursor for higher olefins, or as a precursor for linear internal olefins (LIOs) formed through double bond isomerization. LAOs are also sometimes directly incorporated in drilling fluids, surfactants, lubricants, and detergents, for example.

LAOs may be synthesized by several different processes starting from low molecular weight feedstock materials. The primary route for synthesizing LAOs is ethylene oligomerization, of which there are several synthetic variants that may be mediated using different Ziegler-type catalysts. Depending on the particular Ziegler-type catalyst and the synthetic conditions, ethylene oligomerization reactions may form a range of homologous LAOs (i.e., $C_{2n}H_{2n}$, where n is a positive integer greater than or equal to 2), or a predominant LAO (e.g., 1-butene, 1-hexene, 1-octene, or 1-decene) may be produced. When multiple LAOs are formed, the product distribution of the LAO blend may follow a Shulz-Flory distribution, with the distribution being arranged about a central molecular weight. When a range of LAOs is produced, fractional distillation processes are frequently employed to separate the LAOs into desired fractions comprising individual LAOS. Such processes are commonly referred to as full-range or wide-range LAO synthesis processes.

One difficulty associated with ethylene oligomerization processes mediated by Ziegler-type catalysts is the formation of insoluble higher oligomers and polymers of ethylene (i.e., polyethylene) that may lead to system fouling and eventual shutdown for cleaning. The term "polymer" is used hereinafter to refer equivalently to both insoluble oligomers and polymers. In addition, such polymers accumulate in the higher molecular weight (higher boiling) fractions of the desired LAOs and may lower the value or utility of those fractions for various applications.

Most often, polymer formation during ethylene oligomerization is not a consequence of the Shulz-Flory distribution. Rather, small amounts of water in the reactor system degrade the quality of the catalyst and lead to polymer formation, rather than a desired distribution of lower molecular weight LAOs or substantially a single LAO, as described in U.S. Pat. No. 4,966,874, for example. U.S. Pat. No. 6,576,721 describes a LAO synthetic process in which the water content of a recycled solvent stream is limited to the low single-digit parts per million (ppm) range in order to decrease polymer formation. Although many industrial synthetic processes may be satisfactorily conducted using recycled solvents having a water content in this range, such water concentrations in the solvent may still lead to excessive polymer formation during ethylene oligomerization reactions. More rigorous process controls than are presently employed during LAO syntheses may be needed to limit water concentrations in the recycled solvent to the parts per billion (ppb) range to address polymer formation more effectively. Benefits of lowering polymer formation during ethylene oligomerization may include, but are not limited to, minimizing process downtime, improving LAO product quality, and promoting energy efficiency of the separation processes employed.

SUMMARY

In some embodiments, the present disclosure provides methods for processing recycled solvent during linear alpha olefin (LAO) syntheses. The methods comprise: catalytically reacting ethylene in a reactor under oligomerization reaction conditions in the presence of a solvent and a Ziegler-type catalyst to form a product stream comprising one or more $C_{2n}H_{2n}$ linear alpha olefins (LAOS) and the solvent, the product stream comprising at least 1-hexene; obtaining a higher LAO-enriched stream by removing residual ethylene and $C_4$ LAOs from the product stream, the higher LAO-enriched stream comprising $C_{6+}$ LAOs and the solvent; separating the 1-hexene from the higher LAO-enriched stream as an overhead stream from a first distillation column; obtaining separated solvent as a side stream from the first distillation column or as a side stream from a first of one or more downstream distillation columns; and returning the separated solvent to the reactor within a recycled solvent stream, the recycled solvent stream passing through one or more driers before returning to the reactor. Variable n is a positive integer greater than or equal to 2. The solvent is provided to the reactor from a recycled solvent stream having a water content such that a mole ratio of the Ziegler-type catalyst to water in the reactor is about 1000:1 or more.

In some embodiments, the present disclosure provides methods for processing recycled solvent during linear alpha olefin (LAO) syntheses using one or more dividing wall columns. The methods comprise: providing ethylene, a Ziegler-type catalyst, and a solvent to a reactor; catalytically reacting the ethylene in the reactor under oligomerization reaction conditions to form a product stream comprising one or more $C_{2n}H_{2n}$ linear alpha olefins (LAOs), residual ethylene, residual Ziegler-type catalyst, and the solvent, the product stream comprising at least 1-hexene; quenching the residual Ziegler-type catalyst in the product stream, and removing the residual ethylene and 1-butene from the product stream to form a higher LAO-enriched stream comprising $C_{6+}$ LAOs and the solvent; separating the 1-hexene from the higher LAO-enriched stream as an overhead stream from a first distillation column and a bottoms stream comprising $C_{8+}$ LAOs from the first distillation column; obtaining separated solvent as a side stream from the first distillation column or as a side stream from one of one or more downstream distillation columns; and returning the separated solvent to the reactor within a recycled solvent stream, the recycled solvent stream passing through one or more driers before returning to the reactor. At least one of the first distillation column or one or more of the one or more downstream distillation columns is a dividing wall column and the separated solvent is obtained from a dividing wall column. Variable n is a positive integer greater than or equal to 2. The solvent is provided to the reactor from a recycled solvent stream having a water content such that a mole ratio of the Ziegler-type catalyst to water in the reactor is about 1000:1 or more.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

The present disclosure generally relates to syntheses of linear alpha olefins and, more specifically, to methods for limiting the amount of water present in a recycled solvent during linear alpha olefin syntheses.

As discussed above, linear alpha olefins (LAOS) are most frequently synthesized though ethylene oligomerization using a Ziegler-type catalyst. A range of homologous LAOs or a predominant LAO may be formed depending on the particular catalyst and the reaction conditions. One issue accompanying LAO syntheses taking place through ethylene oligomerization is the co-production of polymers, which may form in the presence of very small amounts of water in the reactor system. Polymer formation degrades the LAO product quality and may eventually lead to system down-time. The role of water in polymer formation during LAO syntheses is well known. Consequently, continuous LAO syntheses may be conducted using a recycled solvent stream having maximal water concentrations in the single-digit parts per million (ppm) range in order to limit polymer formation, as described in U.S. Pat. No. 6,576,721. While sufficiently low for many industrial synthetic processes, water contents in this range may still lead to excessive polymer formation during LAO syntheses.

The present disclosure demonstrates that a catalyst-to-water mole ratio (i.e., a $Zr:H_2O$ ratio in the case of a Zr-based Ziegler-type catalyst) of about 1000:1 or more in a recycled solvent stream may produce LAOs with a much lower incidence of polymer formation than occurs at single-digit ppm water concentrations. The above catalyst-to-water mole ratio corresponds to a water concentration of about 50 ppb or lower in the recycled solvent stream used in the reaction (assuming an ethylene:solvent weight/weight ratio of 1:1).

The present disclosure describes how multiple approaches may be employed to achieve a water content in the recycled solvent stream of continuous LAO syntheses such that polymer formation is limited to a manageable, if not non-existent level. Namely, the LAO syntheses disclosed herein feature a recycled solvent stream that is withdrawn as a side stream from a distillation column used in separating individual LAO fractions. Withdrawal of the solvent as a side stream may limit the amount of co-distilled water that is present in the distillate when compared to that obtained by distillation as an overhead stream. Potential water sources during distillation may include, for example, steam leaks in heat exchangers or reboilers, cooling water leaks in condensers or process coolers, pump seal flushes, and/or admixed water carried with the solvent following catalyst quenching. Regardless of source, the water typically distills in the overhead stream. Obtaining the recycled solvent as a side stream, therefore, significantly reduces the risk of introducing trace amounts of water in the recycled solvent stream provided to the reactor. In addition, a solvent having a low affinity for water, particularly when obtained from a non-overhead stream, may reduce capital equipment requirements and/or the frequency at which driers need to be regenerated.

In addition to separating the solvent as a side stream, the LAO syntheses disclosed herein further employ other various measures for limiting and/or mitigating the possible presence of water in the recycled solvent stream. One further approach for limiting the presence of water according to the present disclosure is employing a solvent having an innate low affinity for water (i.e., low solubility of water in the solvent), such as below about 600 ppm at 25° C., and particularly below about 150 ppm at 25° C. for aliphatic hydrocarbon solvents. Using a solvent with an innate low affinity for water limits the amount of admixed water carried with the solvent into the distillation column, thereby lowering the amount of water available for potentially co-distilling with the solvent and entering the recycled solvent stream. In additional further approaches, the recycled solvent stream obtained following distillation may be passed through one or more driers before being returned to the reactor. The one or more driers may mitigate the presence of any water that does manage to co-distill and enter the recycled solvent stream. Thus, the present disclosure describes an advantageous combined approach for limiting the introduction of water to the reactor of LAO synthetic processes, thereby affording potential benefits such as, for example, a lower incidence of polymer formation, improved LAO product quality, and less system downtime. In a particular aspect of product quality, a decreased potential for formation of heteroatom-containing byproducts may be realized by keeping the water content as low as possible.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_{n1}$" refers to hydrocarbon(s) or a hydrocarbyl group having n carbon atom(s) per molecule or group, wherein $n_1$ is a positive integer. Such hydrocarbon compounds may be one or more of linear, branched, cyclic, acyclic, saturated, unsaturated, aliphatic, or aromatic.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. "Hydrocarbyl groups" may be optionally substituted, in which the term "optionally substituted" refers to replacement of at least one hydrogen atom or at least one carbon atom with a heteroatom or heteroatom functional group. Heteroatoms may include, but are not limited to, B, O, N, S, P, F, Cl, Br, I, Si, Pb, Ge, Sn, As, Sb, Se, and Te. Hydrocarbyl groups therefore may include alkyl, alkenyl, alkynyl, aryl, heteroaryl, cycloalkyl, heterocyclyl, and the like, any of which may be optionally-substituted.

The term "alkyl" refers to a hydrocarbyl group having no unsaturated carbon-carbon bonds, and which may be optionally substituted. The term "alkyl" may be used synonymously with the term "paraffinic."

The term "alkenyl" refers to a hydrocarbyl group having a carbon-carbon double bond, and which may be optionally substituted. The terms "alkene" and "olefin" are used synonymously herein. Similarly, the terms "alkenic" and "olefinic" are used synonymously herein. Unless otherwise noted, all possible geometric isomers are encompassed by these terms.

The terms "aromatic" and "aromatic hydrocarbon" refer to a hydrocarbon or hydrocarbyl group having a cyclic arrangement of conjugated pi-electrons that satisfy the Hückel rule. The term "aryl" is equivalent to the term "aromatic" as defined herein. The term "aryl" refers to both aromatic compounds and heteroaromatic compounds, either of which may be optionally substituted. Both mononuclear and polynuclear aromatic compounds are encompassed by these terms.

The terms "linear" and "linear hydrocarbon" refer to a hydrocarbon or hydrocarbyl group having a continuous carbon chain without side chain branching.

The term "linear alpha olefin (LAO)" refers to an alkenic hydrocarbon bearing a carbon-carbon double bond at a terminal (end) carbon atom of the main carbon chain.

The terms "branch," "branched" and "branched hydrocarbon" refer to a hydrocarbon or hydrocarbyl group having a linear main carbon chain in which a hydrocarbyl side chain extends from the linear main carbon chain.

The terms "unbranched" and "normal" refer to a straight-chain hydrocarbon or hydrocarbyl group.

The term "higher LAO" refers to LAOs having at least 6 carbon atoms.

The term "individual LAO" refers to a distillation fraction consisting essentially of a single LAO.

Processes for forming LAOs using a recycled solvent stream according to the present disclosure may comprise: catalytically reacting ethylene in reactor under oligomerization reaction conditions in the presence of a solvent and a Ziegler-type catalyst to form a product stream comprising one or more $C_{2n}H_{2n}$ LAOs and the solvent (n specifies the chain length of the LAOs and is a positive integer greater than or equal to 2), the product stream comprising at least 1-hexene; obtaining a higher LAO-enriched stream by removing residual ethylene and $C_4$ LAOs from the product stream, the higher LAO-enriched stream comprising $C_{6+}$ LAOs and the solvent; separating the 1-hexene from the higher LAO-enriched stream as an overhead stream from a first distillation column; obtaining separated solvent as a side stream from the first distillation column or as a side stream from a first of one or more downstream distillation columns; and returning the separated solvent to the reactor within a recycled solvent stream, the recycled solvent stream passing through one or more driers before returning to the reactor. The solvent is provided to the reactor from a recycled solvent stream having a water content such that a mole ratio of the Ziegler-type catalyst to water in the reactor is about 1000:1 or more, or about 2000:1 or more, or about 3000:1 or more, or about 5000:1 or more, or about 10,000:1 or more.

Figure 1A:
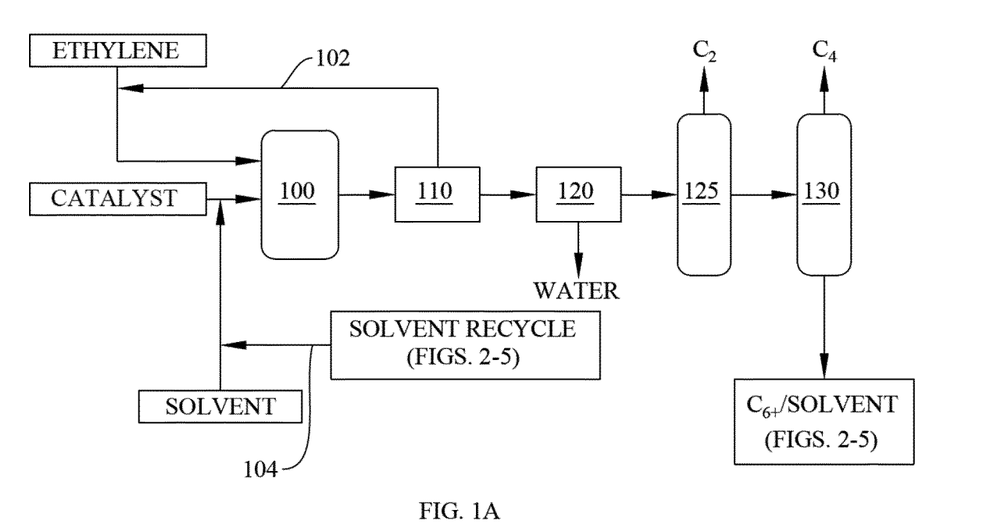
FIGS. 1A and 1B show block diagrams illustrating various operations that may be performed in the course of forming and isolating LAOS, and which may be implemented with one or more embodiments of the present disclosure.
Figure 1B:
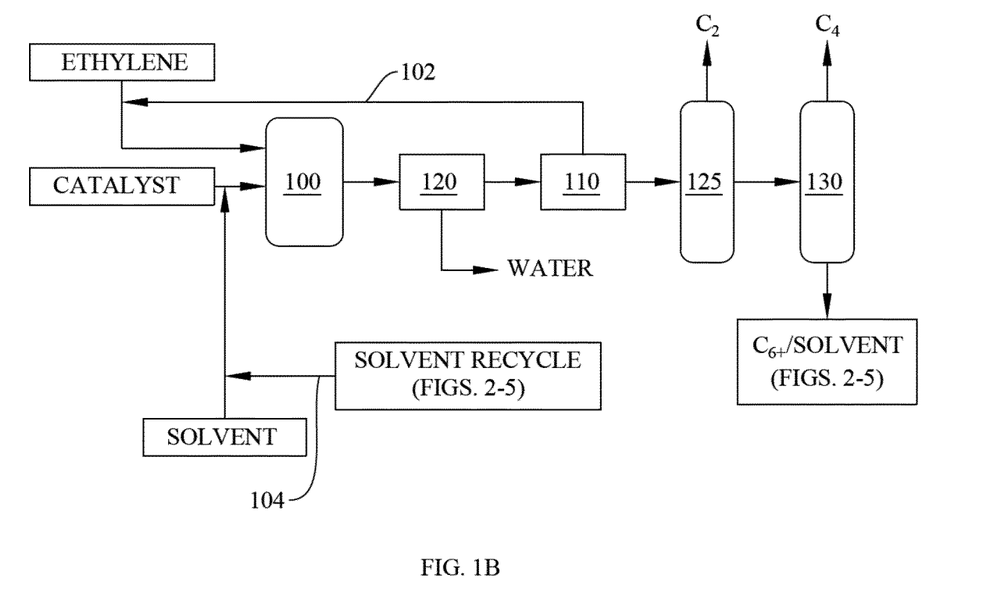

Before providing further description of suitable process conditions and variants of Ziegler-type catalysts, illustrative LAO syntheses will be described in additional detail with reference to FIGS. 1A and 1B. FIGS. 1A and 1B show block diagrams illustrating various operations that may be performed in the course of forming and isolating LAOS, and which may be implemented with one or more embodiments of the present disclosure. Process details directed to obtaining separated solvent as a side stream from a distillation column and returning a recycled solvent stream to a reactor for further LAO synthesis is described below in reference to subsequent FIGS. 2-5. It is to be appreciated that various features in the FIGS. may be shown in general terms and/or be described in brief in order to focus more succinctly on the separation and solvent recycling aspects of the present disclosure referenced above. For example, it is to be understood that components such as reboilers, pumps and like equipment are not shown in the FIGS. in order to focus more succinctly on aspects of the present disclosure, but it is to be understood that such components may be present and implemented in any suitable fashion in a physical system, as will be appreciated by one having ordinary skill in the art.

As shown in FIG. 1A, ethylene, catalyst and solvent are provided to reactor 100 via corresponding supply lines to form LAOs therein. At least a portion of the ethylene and the solvent may be recycled and provided by ethylene recycle stream 102 and recycled solvent stream 104, respectively. Ethylene recycle stream 102 and/or recycled solvent stream 104 may pass through one or more driers (not shown in FIG. 1A) prior to returning the ethylene or solvent to reactor 100. The product stream from reactor 100 next passes to ethylene recovery unit 110, whereupon ethylene is removed from the product stream as an overhead stream and is returned to reactor 100 via ethylene recycle line 102. The product stream then proceeds from ethylene recovery unit 110 to catalyst deactivation unit 120, wherein catalyst deactivation occurs and any water used in or formed in the course of catalyst deactivation is removed. Small amounts of admixed water may remain in the LAOs and solvent following catalyst deactivation. Remaining traces of ethylene and other inert hydrocarbons (e.g., methane and ethane byproducts) in the product stream may optionally be removed in lead distillation column 125. The $C_4$ LAOs formed during the LAO synthesis (i.e., 1-butene) are next removed from the product stream in an overhead stream from light alkene distillation column 130, thereby providing a higher LAO-enriched stream as a bottoms stream. The higher LAO-enriched stream comprises $C_{6+}$ LAOs, solvent and residual water, if present. The higher LAO-enriched stream is then provided to multiple downstream distillation columns for separation of individual LAOs from one another and from solvent, as described further below in reference to FIGS. 2-5.

In a process variation also compatible with the present disclosure, catalyst deactivation may precede ethylene recovery, as shown in FIG. 1B. When catalyst deactivation precedes ethylene recovery, there may be less need for further ethylene removal using lead distillation column 125. However, further ethylene removal may take place, if desired or warranted under particular process conditions. Hence, lead distillation column 125 may be optionally omitted in such process configurations.

Ethylene may be provided to reactor 100 as a substantially pure ethylene feed or as a mixture of ethylene with one or more inert gases, such as nitrogen, helium or argon. Methane, ethane and other saturated hydrocarbon gases are also suitably inert in the LAO synthesis processes of the present disclosure and may also be present in the ethylene provided to reactor 100. The methane and ethane may be present in commercially sourced ethylene, for example. Ethylene obtained from ethylene recycle stream 102 may contain substantially pure ethylene or substantially pure ethylene and a limited amount of $C_{3+}$ alkenes, including $C_{4+}$ LAOs (e.g., <0.1 wt. % $C_{4+}$ LAOs), and/or inert gases.

Oligomerization reaction conditions suitable for synthesizing LAOs in reactor 100 may further include temperature and pressure conditions such as a temperature from about 50° C. to about 250° C. (e.g., about 170° C.), and a pressure of about 3450 kPa to about 34500 kPa or a pressure of about 6900 kPa to about 24100 kPa. In some embodiments, the temperature and pressure may be such that the ethylene is in a supercritical state, in which case the Ziegler-type catalyst and solvent may be homogenously mixed with the ethylene. The ratio of solvent to ethylene entering the reactor may range from about 0.2:1 to about 3.0:1 or about 0.5:1 to about 1.5:1, with equal volumes of solvent and ethylene being used in some embodiments.

Reactor configurations suitable for synthesizing LAOs according to the disclosure herein are not considered to be particularly limited. Suitable reactor configurations may include, for example, a fluidized bed, an ebullated bed, a slurry bed, a trickle bed, a plug flow reactor, a stirred tank reactor, a turbulent flow reactor, or any other reactor type suitable for forming a product stream. A residence time within the reactor may range between about 5 minutes to about 90 minutes, or about 5 minutes to about 15 minutes, or about 10 minutes to about 60 minutes, or about 20 minutes to about 80 minutes. Furthermore, because linearity of the alpha olefins tends to decrease with increasing carbon chain length and increasing ethylene conversion, the amount of ethylene converted during each transit through the reactor may range between about 50% to about 80%, such as from about 55% to about 70%, or from about 60% to about 65%. The conversion rate is commonly called the "per pass conversion."

Suitable solvents for forming LAOs using Ziegler-type catalysts may include various hydrocarbon solvents. Illustrative solvents that may be used when synthesizing LAOs include, for example, mineral oil; straight or branched-chain hydrocarbons (e.g., propane, isobutane, butane, pentane, isopentane, hexane, isohexane, heptane, isoheptane, octane, dodecane, 2,2-dimethylpentane, and 2,2,4-trimethylpentane); cyclic and alicyclic hydrocarbons (e.g., cyclohexane, cycloheptane, cyclooctane, methylcyclopentane; methylcyclohexane, and methylcycloheptane); perhalogenated hydrocarbons such as perfluorinated $C_4$-$C_{10}$ alkanes; aromatic hydrocarbons (e.g., benzene, toluene, ethylbenzene, mesitylene, p-xylene, m-xylene, o-xylene, chorobenzenes), and any combination thereof. Additional considerations for selection of a suitable solvent may be dictated by the location where solvent separation takes place, as explained in further detail below in reference to FIGS. 2-5.

Suitable Ziegler-type catalysts may include zirconium-, titanium-, magnesium- or chromium based-catalysts. The catalyst quantity used during LAO syntheses is conveniently expressed by the weight ratio of ethylene feed to the metal in the catalyst (e.g., Ti, Mg, Zr or Cr). LAO syntheses may, according to various embodiments, be conducted at an ethylene-to-metal weight ratio ranging between about 10,000:1 to about 120,000:1 or between about 25,000:1 to about 35,000:1. Moreover, as described further herein, the catalyst quantity may also be characterized by a catalyst-to-water mole ratio of greater than about 1000:1, or greater than about 2000:1, or greater than about 5000:1, or greater than 10,000:1. Alternately, the catalyst quantity may also be characterized by a catalyst-to-water mole ratio (e.g., Ziegler-type catalyst to water mole ratio) in the reactor of about 1000:1 or more, or about 2000:1 or more, or about 3000:1 or more, or about 5000:1 or more, or about 10,000:1 or more.

Some Ziegler-type catalysts may comprise homogeneous, single-site chromium catalysts. Such catalysts may be formed from a chromium source in combination with a heterocyclic, di-aryl, or phosphorus compound such as a pyrrole, pyridyl or pyridyl-phosphino compound, along with an aluminum activator such as methyl alumoxane (MAO) or modified methyl alumoxane (MMAO). Such catalysts may be pre-formed when provided to the reactor, or they may be formulated on-the-fly (inline) by combining the catalyst components in the supply line feeding the catalyst to the reactor.

Some Ziegler-type catalysts suitable for forming LAOs may be two-component zirconium-based catalysts. In more specific embodiments, the first component may be an adduct of a zirconium halide (i.e., $ZrCl_aBr_b$, wherein each of a and b is 0, 1, 2, 3 or 4 and a+b=4) with an organic compound having up to about 30 carbon atoms and that is selected from the group consisting of esters, ketones, ethers, amines, nitriles, anhydrides, acid chlorides, amides and aldehydes, and second component may be an alkylaluminum or alkylzinc compound selected from the group consisting of $R_2AlX$, $RAlX_2/R_3Al_2X_3$, $R_3Al$, and $R_2Zn$, in which R is a $C_1$-$C_{20}$ alkyl group and X is Cl or Br. The zirconium halide adduct (first component) may include a mole ratio of the organic compound to zirconium ranging between about 0.9:1 to about 2:1. In such embodiments, the oligomerization reaction may be conducted in the presence of about 10-50 ppm of oxygen relative to the amount of ethylene that is present. Such catalysts may likewise be pre-formed when provided to the reactor, or they may be formulated on-the-fly (inline) by combining the catalyst components in the supply line feeding the catalyst to the reactor.

In more particular embodiments of such zirconium-based Ziegler-type catalysts, the organic compound may be an ester having a formula of $R^1COOR^2$, wherein $R^1$ and $R^2$ are each $C_1$-$C_{30}$ alkyl, aryl, alkaryl, or aralkyl groups, with the proviso that $R^1$ may also be hydrogen. $R^1$ and $R^2$ taken together may also represent a cycloaliphatic group and the ester may be a lactone such as γ-butyrolactone or a phthalide. In more particular embodiments, alkyl esters having about 6 to about 16 carbon atoms may be desirable, such as n-hexyl acetate, n-heptyl acetate, n-octyl acetate, n-nonyl acetate, n-decyl acetate, isohexyl acetate, isodecyl acetate and the like, which may form dimeric equimolar adducts with $ZrCl_4$ and exhibit high catalyst solubility in common solvents suitable for forming LAOS.

When using a zirconium-based Ziegler-type catalyst for LAO syntheses, the relative amounts of the first component to the second component may vary over a wide range. In some embodiments, a mole ratio of the second component to the first component may range between about 1:1 and about 50:1 or from about 10:1 to about 25:1.

Catalyst deactivation within the product stream may take place with a suitable quenching agent, such as a caustic material in a water solution. Suitable quenching agents may include aqueous ammonia, or aqueous alkali metal or alkaline earth metal basic solutions, such as alkali metal or alkaline earth metal hydroxides, oxides, carbonates or bicarbonates. Amine quenching agents (e.g., methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphenylamine, methylphenylamine, trimethylamine, triethylamine, tributylamine, triphenylamine, pyridine, picoline, or 1,5-diamino-2-methylpentane) may be used in other embodiments. Alcohols, carboxylic acids, and phenols may also comprise suitable quenching agents in still other embodiments.

Processes for separating solvent as a side stream following catalyst deactivation will now be described in additional detail, making further reference to FIGS. 2-5 when necessary.

In some embodiments, the separated solvent is obtained as a side stream (middle distillate) from the first distillation column, and $C_{8+}$ LAOs are separated as a bottoms stream from the first distillation column. As mentioned above and explained in further detail below in reference to FIGS. 2 and 3, 1-hexene is separated as an overhead stream from the first distillation column. Such methods may further comprise providing the bottoms stream comprising $C_{8+}$ LAOs to a first of the one or more downstream distillation columns, and separating individual LAO overhead streams from the one or more downstream distillation columns, wherein each of the one or more downstream distillation columns provides a different individual LAO overhead stream (i.e., a LAO having a different carbon count). Process configurations in which a separated solvent is obtained as a side stream from a first distillation column are described in further detail below in reference to FIGS. 2 and 3.

Figure 2:
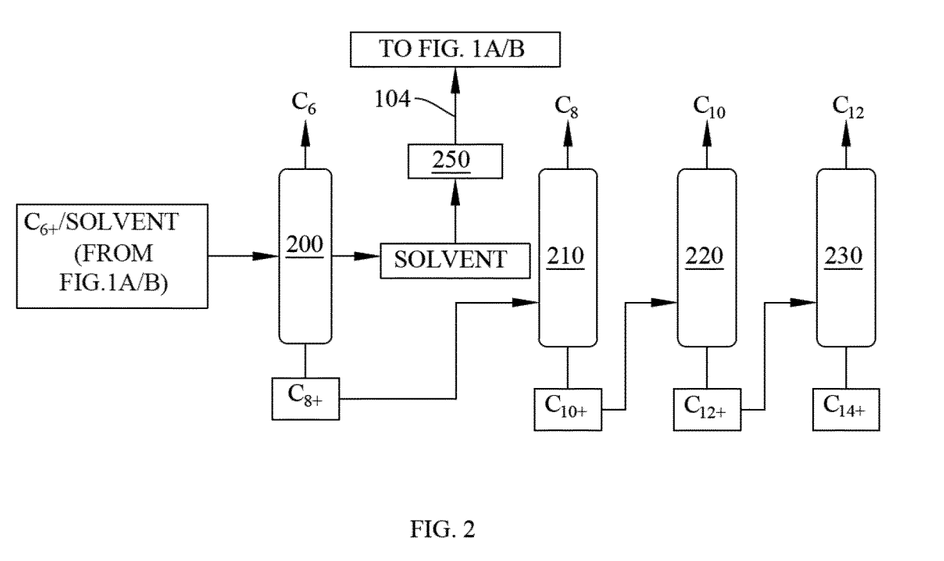
FIG. 2 shows a block diagram detailing processes for separating the solvent of an LAO synthesis as a side stream concurrently with obtaining $C_6$ LAOs as an overhead stream from a distillation column.

FIG. 2 shows a block diagram detailing processes for separating the solvent of an LAO synthesis as a side stream concurrently with obtaining $C_6$ LAOs as an overhead stream from a distillation column. As shown in FIG. 2, a higher LAO-enriched stream comprising $C_{6+}$ LAOs and solvent is introduced to distillation column 200, whereupon $C_6$ LAOs may be separated as an overhead stream and $C_{8+}$ LAOs may be obtained as a bottoms stream. Provided that the solvent has a boiling point residing between that of 1-hexene and 1-octene (i.e., between normal boiling points of 63° C. and 121° C.), a side stream that is at least enriched in the solvent may be obtained from distillation column 200. The $C_{8+}$ LAOs in the bottoms stream may then be passed to downstream distillation column 210, whereupon $C_8$ LAOs may be obtained as an overhead stream and $C_{10+}$ LAOs may be obtained as a bottoms stream. Also linked serially to downstream distillation column 210 are downstream distillation columns 220 and 230. $C_{10}$ and $C_{12}$ LAOs may be obtained as an overhead stream from downstream distillation columns 210 and 220, respectively, with $C_{12+}$ LAOs and $C_{14+}$ LAOs being obtained as bottoms streams, as shown in FIG. 2. Although further LAO separation is not shown in FIG. 2, it is to be appreciated that additional downstream distillation columns linked in series may be employed to isolate individual LAOs up to a desired carbon count.

In the configuration shown in FIG. 2, an overhead stream comprising a single LAO is obtained from distillation column 200 ($C_6$ LAOs) and from each of downstream distillation columns 210, 220 and 230. Purified or enriched solvent is separated as a side stream from distillation column 200. As an alternative to using only two-product distillation columns (i.e., a distillation column that only provides an overhead stream and a bottoms stream unless a side stream is withdrawn) in each location, as shown in the configuration of FIG. 2, some embodiments of the present disclosure may utilize one or more dividing wall columns in order to realize more effective separation of individual LAOs and solvent from one another, in addition to providing the advantage of reduced capital expenditure for a reactor system, as explained hereinafter. Namely, in such configurations, at least one of the first distillation column or one or more of the one or more downstream distillation columns may be a dividing wall column. In more specific implementations of such configurations, the separated solvent may be obtained as a side stream from a dividing wall column. The dividing wall may promote more effective separation of the side stream, as described herein.

The dividing wall in a dividing wall column of the present disclosure may have a height ranging from about 25% to about 95% of the overall distillation column height. A single dividing wall defines two chambers within the distillation column. Multiple dividing walls may also be present in a dividing wall column of the present disclosure to define additional chambers and thereby promote even more effective separation. The chambers defined within a dividing wall column may contain any combination of a plurality of distillation plates, structured corrugated metal packing, or randomly positioned loose packing materials. The vertical position of the dividing wall(s) within the dividing wall column may be such that a side stream is obtained from the distillation column at a desired height, so as to promote satisfactory separation of the side stream from higher and lower boiling LAOS. Further details of the operational principles of dividing wall columns are provided hereinafter.

A feed stream is provided to a dividing wall column at a location below the top and above the bottom of the dividing wall. The feed stream undergoes separation in the chamber it enters, but it is blocked from directly entering the chamber opposite the point of entry, thereby improving separation efficiency. Instead, an overhead stream may be obtained from the entering chamber, and the column bottoms are therefore lean in the component(s) removed in the overhead stream. Upon volatilizing the column bottoms, the vapor phase in the chamber opposite the point of feed stream entry is also lean in the component(s) removed in the overhead stream, thereby allowing the side stream to be obtained in a more pure state.

Figure 3:
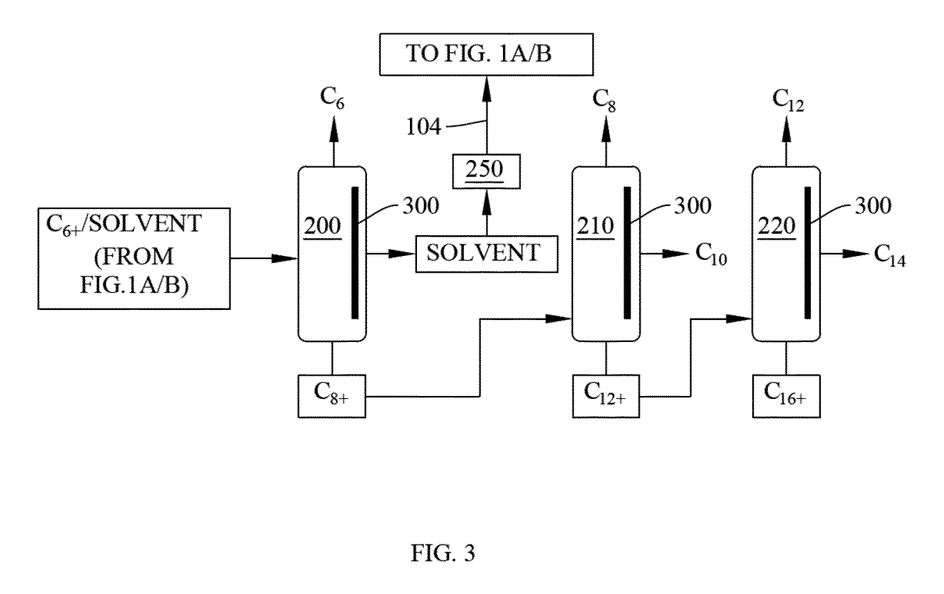
FIG. 3 shows a block diagram detailing processes for separating the solvent of an LAO synthesis as a side stream concurrently with obtaining $C_6$ LAOs as an overhead stream from a dividing wall column.

FIG. 3 shows a block diagram detailing processes for separating the solvent of an LAO synthesis as a side stream concurrently with obtaining $C_6$ LAOs as an overhead stream from a dividing wall column. In the configuration shown in FIG. 3, distillation column 200 and downstream distillation columns 210 and 220 each incorporate dividing wall 300 there within. It is to be understood, however, that alternative configurations may feature a two-product distillation column at any of the distillation column locations instead of one incorporating dividing wall 300. Given the benefit of the present disclosure and an understanding of the separation features afforded by dividing wall columns, as presented hereinafter, one having ordinary skill in the art may readily determine the location where a given LAO or solvent may be obtained from a particular distillation column configuration.

Referring again to FIG. 3, $C_6$ LAOs are again obtained as the overhead stream from distillation column 200 and solvent is likewise obtained as the side stream from distillation column 200, provided that the solvent has a boiling point residing between that of 1-hexene and 1-octene. The $C_{8+}$ LAOs obtained as the bottoms stream from distillation column 200 are similarly provided to downstream distillation column 210. Instead of obtaining a single isolated LAO fraction from downstream distillation column 210, as in the configuration of FIG. 2, two isolated LAO fractions may be obtained from downstream distillation column when utilizing dividing wall 300. Namely, $C_8$ LAOs are obtained as the overhead stream and $C_{10}$ LAOs are obtained as a side stream from downstream distillation column 210, and $C_{12+}$ LAOs are obtained as the bottoms stream. Similarly, by providing the $C_{12+}$ LAOs to downstream distillation column 220, $C_{12}$ LAOs and $C_{14}$ LAOs may be obtained as the overhead stream and side stream, respectively, from downstream distillation column 220, and $C_{16+}$ LAOs may be obtained as the bottoms stream. It is again to be appreciated that further downstream distillation columns linked in series may be incorporated in the configuration of FIG. 3 to facilitate isolation of additional individual LAOs up to a desired carbon count.

In view of the foregoing, it can be appreciated that utilizing a dividing wall column as a first distillation column may facilitate solvent separation as a side stream therefrom. Moreover, by utilizing a dividing wall column as at least one of the downstream distillation columns, a reactor system having a fixed number of columns may separate more individual LAO fractions compared to one utilizing only two-product distillation columns. Alternately, when fractionating a mixture of LAOs up to a given carbon count by using at least one downstream dividing wall column, fewer overall distillation columns are needed compared to when only two-product distillation columns are used.

When the separated solvent is obtained as a side stream from the first distillation column, similar considerations for selecting a suitable solvent apply to both of the above column configurations (i.e., configurations in which the first column is a two-product distillation column or a dividing wall column). In either configuration wherein the separated solvent is obtained as a side stream from the first distillation column, the solvent has a boiling point ranging between that of 1-hexene (separated as the overhead stream) and 1-octene (separated with other $C_{8+}$ LAOs as the bottoms stream). More suitably, the solvent may be separated from the boiling points of 1-hexene (63° C.) and 1-octene (121° C.) in order to promote more effective separation. Accordingly, in more specific embodiments, suitable solvents may have boiling points that are separated from the boiling points of 1-hexene and 1-octene by at least about 5° C., or at least about 8° C. in order to facilitate separation of the solvent as a side stream from a distillation column having a reasonable height. Thus, in some embodiments, solvents suitable for being separated as a side stream from the first distillation column may have normal boiling points ranging from 68° C. to 116° C. Suitable hydrocarbon solvents having a normal boiling point in this range may include, but are not limited to methylcyclopentane, cyclohexane, isoheptane, 2,2-dimethylpentane, 2,2,4-trimethylpentane, methylcyclohexane, toluene, and any combination thereof. These solvents further have a low affinity for water, such as below about 600 ppm for aromatic solvents (543 ppm for toluene at 25° C.) and below about 150 ppm at 25° C. for aliphatic hydrocarbon solvents, which may provide further advantages for limiting water in the solvent recycle stream, as discussed further above.

It is to be further appreciated that while the solvent selections herein may be described in terms of their normal boiling points, it is to be understood that the separation processes of the present disclosure are not limited to atmospheric pressure distillation processes. Any of the separation processes described here may be conducted at sub-atmospheric distillation pressures, such as from about 0.1 torr to about 750 torr. In the case of sub-atmospheric distillation pressures, the LAOs and the solvent distill at lower temperatures, with the boiling points being a function of the actual pressure employed. Provided that the solvent boiling point remains between that of 1-hexene and 1-octene at the sub-atmospheric pressure, the separation principles described hereinabove continue to apply.

The separated solvent may be obtained as a side stream in locations other than those described above and depicted in detail in FIGS. 2 and 3. In some embodiments, the separated solvent may be obtained as a side stream from a first of the one or more downstream distillation columns, with 1-octene being separated as an overhead stream from the first of the one or more downstream distillation columns and $C_{10+}$ LAOs being separated as a bottoms stream from the first of the one or more downstream distillation columns. Configurations in which a separated solvent is obtained as a side stream from a first of the one or more downstream distillation columns are described in further detail below in reference to FIGS. 4 and 5. Like the configurations depicted in FIGS. 2 and 3, configurations in which solvent is recycled from the first of the one or more downstream distillation columns may further comprise separating individual LAO overhead streams from the one or more downstream distillation columns, wherein each of the one or more downstream distillation columns provides a different individual LAO overhead stream.

Figure 4:
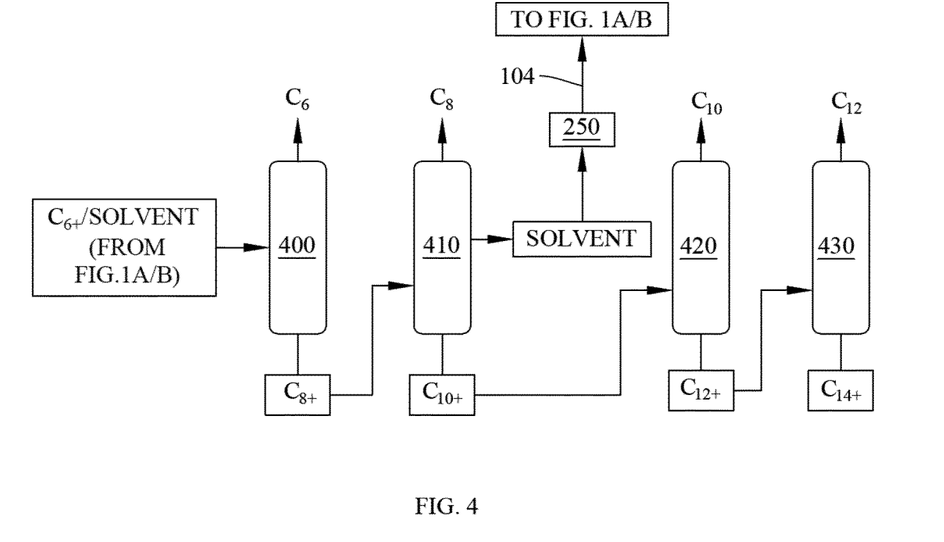
FIG. 4 shows a block diagram detailing processes for separating the solvent of an LAO synthesis as a side stream concurrently with obtaining $C_8$ LAOs as an overhead stream from a distillation column downstream from a distillation column separating $C_6$ LAOs.

FIG. 4 shows a block diagram detailing processes for separating the solvent of an LAO synthesis as a side stream concurrently with obtaining $C_8$ LAOs as an overhead stream from a distillation column downstream from a distillation column separating $C_6$ LAOs. As shown in FIG. 4, a mixture of $C_{6+}$ LAOs and solvent is introduced to distillation column 400, whereupon $C_6$ LAOs may be separated as an overhead stream and $C_{8+}$ LAOs and solvent are obtained in a bottoms stream. For solvents having a boiling point above that of 1-octene, no solvent separation takes place in distillation column 400 in the configuration shown in FIG. 4. The bottoms stream comprising $C_{8+}$ LAOs and solvent is provided to downstream distillation column 410, which is further serially linked to downstream distillation columns 420 and 430. $C_8$ LAOs are obtained as an overhead stream from downstream distillation column 410. Provided that the solvent has a boiling point residing between that of 1-octene and 1-decene (i.e., between normal boiling points of 121° C. and 172° C.), a side stream that is at least enriched in the solvent may be obtained from distillation column 410. $C_{10+}$ LAOs are obtained as a bottoms stream from distillation column 410 and are then passed to downstream distillation column 420, whereupon $C_{10}$ LAOs may be obtained as an overhead stream and $C_{12+}$ LAOs may be obtained as a bottoms stream. Similarly, downstream distillation column 430 may separate an overhead stream comprising $C_{12}$ LAOs and provide $C_{14+}$ LAOs as a bottoms stream. Although further LAO separation is not shown in FIG. 4, it is to be appreciated that additional downstream distillation columns linked in series may be employed to isolate individual LAOs up to a desired carbon count.

In the configuration shown in FIG. 4, an overhead stream comprising a single LAO is obtained from distillation column 400 and from each of downstream distillation columns 410, 420 and 430. Purified or enriched solvent is obtained as a side stream from downstream distillation column 410. As an alternative to using only two-product distillation columns, as shown in the configuration of FIG. 4, some embodiments of the present disclosure may utilize one or more dividing wall columns in order to realize more effective separation of individual LAOs and solvent from one another, in addition to other benefits which have been described in more detail above. Namely, in such configurations, at least one of the first distillation column or one or more of the one or more downstream distillation columns may be a dividing wall column. In more specific configurations, the first distillation column may be a two-product distillation column and the one or more downstream distillation columns may be a dividing wall column. In still more specific implementations of such configurations, the separated solvent may be obtained as a side stream from one of the dividing wall columns.

Figure 5:
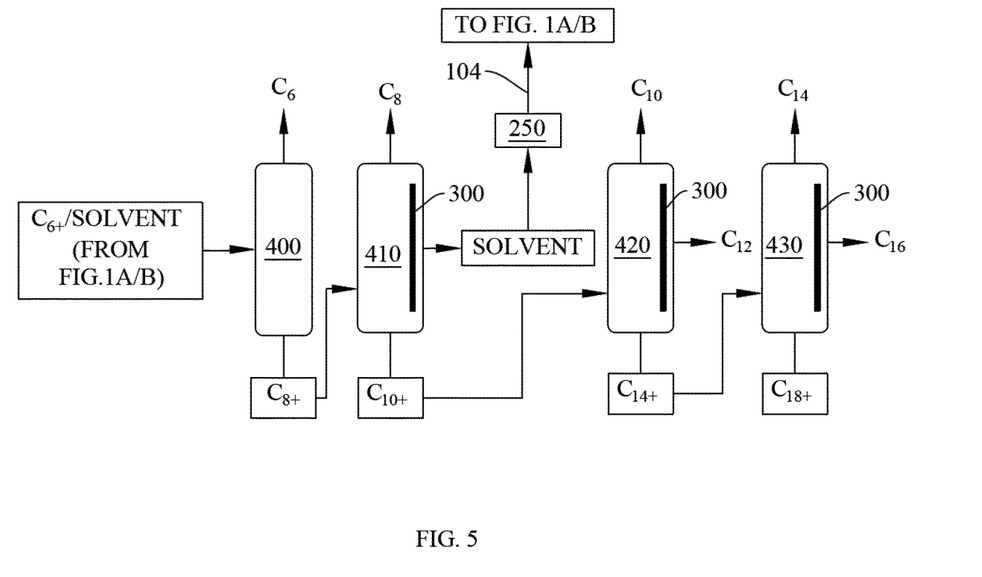
FIG. 5 shows a block diagram illustrating processes for separating the solvent of an LAO synthesis as a side stream concurrently with obtaining $C_8$ LAOs as an overhead stream from a dividing wall distillation column downstream of a distillation column separating $C_6$ LAOS.

FIG. 5 shows a block diagram illustrating processes for separating the solvent of an LAO synthesis as a side stream concurrently with obtaining $C_8$ LAOs as an overhead stream from a dividing wall distillation column downstream of a distillation column separating $C_6$ LAOS. In the distillation configuration shown in FIG. 5, downstream distillation columns 410, 420 and 430 each incorporate dividing wall 300, but distillation column 400 does not. As can be appreciated by one having ordinary skill in the art and the benefit of the disclosure herein, incorporating dividing wall 300 within distillation column 400 may change the separation principles depicted in FIG. 5 for obtaining individual LAO fractions and solvent, specifically the locations where each LAO fraction and solvent are obtained. It is to be understood, however, that alternative configurations incorporating dividing wall 300 within distillation column 400 also reside within the scope of the present disclosure, with the understanding that LAO fractions and separated solvent may be obtained from different locations than those depicted in FIGS. 4 and 5. For example, when dividing wall 300 is incorporated within distillation column 400, the solvent needs to have a boiling point residing between that of 1-decene and 1-dodecene in order to be obtained as a side stream from downstream distillation column 410.

Referring again to the configuration depicted in FIG. 5, $C_6$ LAOs are again obtained as the overhead stream from distillation column 400, with $C_{8+}$ LAOs and solvent being obtained as a bottoms stream, provided that the solvent has a boiling point at least equal to that of 1-octene. The $C_{8+}$ LAOs and solvent obtained as the bottoms stream from distillation column 400 is provided to downstream distillation column 410, which incorporates dividing wall 300. Provided that the solvent has a boiling point residing between that of 1-octene and 1-decene, 1-octene is obtained as an overhead stream from downstream distillation column 410, separated solvent is obtained as a side stream from downstream distillation column 410, and $C_{10+}$ LAOs are separated as a bottoms stream. Continuing from downstream distillation column 410, the $C_{10+}$ LAOs are passed to downstream distillation column 420, which also incorporates dividing wall 300. $C_{10}$ LAOs are obtained as an overhead stream from downstream distillation column 420, $C_{12}$ LAOs are obtained as a side stream, and $C_{14+}$ LAOs are obtained as bottoms stream. Similarly, the $C_{14+}$ LAOs are passed to downstream distillation column 430 to provide $C_{14}$ LAOs as an overhead stream, $C_{16}$ LAOs as a side stream, and $C_{18+}$ LAOs as a bottoms stream.

It is again to be appreciated that further downstream distillation columns linked in series may be incorporated in the configuration of FIG. 5 to isolate additional individual LAOs up to a desired carbon count. Thus, by utilizing a dividing wall column as at least one of the downstream distillation columns, a reactor system having a fixed number of columns may separate more individual LAO fractions compared to one utilizing only two-product distillation columns. Alternately, when fractionating a mixture of LAOs up to a given carbon count, fewer distillation columns are needed when at least one downstream distillation column with a dividing wall is used compared to a reactor system utilizing only two-product distillation columns.

When obtaining the separated solvent as a side stream from the first of the one or more downstream distillation columns, the solvent has a boiling point ranging between that of 1-octene (separated as the overhead stream) and 1-decene (separated with other $C_{10+}$ LAOs as the bottoms stream). More suitably, the solvent may be separated from the boiling points of 1-octene (121° C.) and 1-decene (172° C.) in order to promote more effective separation. In some embodiments, suitable solvents may have boiling points that are separated from the boiling points of 1-octene and 1-decene by at least about 5° C., or at least about 8° C. in order to facilitate separation of the solvent as a side stream from a distillation column (conventional or dividing wall) having a reasonable height. Thus, in some embodiments, solvents suitable for being obtained as a side stream from the first of the one or more downstream distillation columns may have a normal boiling ranging from 126° C. to 167° C. (i.e., the full range between the normal boiling points of 1-octene and 1-decene and factoring in a 5° C. boiling point separation). Suitable solvents having a normal boiling point in this range may include, but are not limited to, p-xylene, m-xylene, o-xylene, ethylbenzene, cyclooctane, 2-methyloctane, nonane, cumene, and any combination thereof. These solvents further have a low affinity for water, such as below 500 ppm for aromatic solvents (440-456 ppm for o-xylene, p-xylene and cumene at 25° C.) and below about 150 ppm at 25° C. for aliphatic hydrocarbon solvents (~80 ppm at 25° C. for cyclooctane and nonane), which may provide further advantages for limiting water in the solvent recycle stream, as discussed further above.

As for the configurations in which solvent separation takes place in the first distillation column (FIGS. 2 and 3), it is to be further appreciated that the separation configuration depicted in FIGS. 4 and 5 is not limited to atmospheric pressure distillation processes. Thus, any of the separation processes described here may be conducted with sub-atmospheric pressure distillation, such as from about 0.1 torr to about 750 torr, in which case the boiling points referenced above may vary as a function of the actual pressure. Provided that the solvent boiling point remains between that of 1-octene and 1-decene at the sub-atmospheric pressure, the separation principles described hereinabove continue to apply to the configuration of FIGS. 4 and 5.

After the solvent is separated from the LAOS, the solvent may be passed through one or more driers as a recycle stream before being returned to the reactor. The solvent in the recycle stream may be obtained from any of the distillation configurations referenced above. Referring again to FIGS. 2-5, with further reference also being made to FIG. 1A, the separated solvent obtained as a side stream (i.e., from distillation column 200 or from downstream distillation column 410) may be passed through one or more driers 250 before being introduced to recycled solvent line 104 for recirculation to reactor 100 (FIG. 1A). Suitable drying agents within one or more driers 250 may include, for example, molecular sieves, an anhydrous salt, a reactive drying agent, and any combination thereof. Examples of molecular sieves that may be effective for water removal include, for example, 3 Å and 4 Å molecular sieves. Examples of anhydrous salts include, for example, anhydrous sodium sulfate, anhydrous magnesium sulfate, calcium chloride, and the like. Examples of reactive drying agents include, for example, sodium metal.

Accordingly, more specific embodiments of the methods of the present disclosure may comprise: providing ethylene, a Ziegler-type catalyst, and a solvent to a reactor; catalytically reacting the ethylene in the reactor under oligomerization reaction conditions to form a product stream comprising a one or more $C_{2n}H_{2n}$ linear alpha olefins (LAOs), unreacted ethylene, residual Ziegler-type catalyst, and the solvent (n is a positive integer greater than or equal to 2), the product stream comprising at least 1-hexene; quenching the residual Ziegler-type catalyst in the product stream, and removing the unreacted ethylene and 1-butene from the product stream to form a higher LAO-enriched stream comprising $C_{6+}$ LAOs and the solvent; separating the 1-hexene from the higher LAO-enriched stream as an overhead stream from a first distillation column and a bottoms stream comprising $C_{8+}$ LAOs from the first distillation column; obtaining separated solvent as a side stream from the first distillation column or as a side stream from one of one or more downstream distillation columns, at least one of the first distillation column and one or more of the one or more downstream distillation columns being a dividing wall column and the separated solvent being obtained from a dividing wall column; and returning the separated solvent to the reactor within a recycled solvent stream, the recycled solvent stream passing through one or more driers before returning to the reactor. The solvent is provided to the reactor from a recycled solvent stream having a water content such that a mole ratio of the Ziegler-type catalyst to water in the reactor is about 1000:1 or more, or about 2000:1 or more, or about 3000:1 or more, or about 5000:1 or more, or about 10,000:1 or more.

In more specific separation configurations employing a dividing wall column, the separated solvent may be obtained as a side stream from the first distillation column, which is a dividing wall column. Any or all of the one or more downstream distillation columns may be dividing wall columns as well. Individual LAO overhead streams may be separated from each of the one or more downstream distillation columns, as described in further detail above. Solvent selection may be in accordance with the description above, wherein the solvent has a boiling point residing between the boiling points of 1-hexene and 1-octene.

In other more specific separation configurations employing a dividing wall column, the separated solvent may be obtained as a side stream from a first of the one or more downstream distillation columns, with at least a first of the one or more downstream distillation columns being a dividing wall column. In such embodiments, the first distillation column may be a two-product distillation column, and any or all of the one or more downstream distillation columns may be a dividing wall column. Alternately, the first distillation column may also be a dividing wall column, but it is to be appreciated that the downstream distribution of LAO products may differ from that depicted in FIGS. 4 and 5. Individual LAO overhead streams may be separated from each of the one or more downstream distillation columns, as described in further detail above. Solvent selection may be in accordance with the description above, wherein the solvent has a boiling point residing between the boiling points of 1-octene and 1-decene.

Embodiments disclosed herein include: A. LAO synthesis methods. The methods comprise: catalytically reacting ethylene in a reactor under oligomerization reaction conditions in the presence of a solvent and a Ziegler-type catalyst to form a product stream comprising one or more $C_{2n}H_{2n}$ linear alpha olefins (LAOS) and the solvent, the product stream comprising at least 1-hexene; wherein n is a positive integer greater than or equal to 2; and wherein the solvent is provided to the reactor from a recycled solvent stream having a water content such that a mole ratio of the Ziegler-type catalyst to water in the reactor is about 1000:1 or more; obtaining a higher LAO-enriched stream by removing residual ethylene and $C_4$ LAOs from the product stream, the higher LAO-enriched stream comprising $C_{6+}$ LAOs and the solvent; separating the 1-hexene from the higher LAO-enriched stream as an overhead stream from a first distillation column; obtaining separated solvent as a side stream from the first distillation column or as a side stream from a first of one or more downstream distillation columns; and returning the separated solvent to the reactor within the recycled solvent stream, the recycled solvent stream passing through one or more driers before returning to the reactor.

B. LAO synthesis methods. The methods comprise: providing ethylene, a Ziegler-type catalyst, and a solvent to a reactor; wherein the solvent is provided to the reactor from a recycled solvent stream having a water content such that a mole ratio of the Ziegler-type catalyst to water in the reactor is about 1000:1 or more; catalytically reacting the ethylene in the reactor under oligomerization reaction conditions to form a product stream comprising one or more $C_{2n}H_{2n}$ linear alpha olefins (LAOs), residual ethylene, residual Ziegler-type catalyst, and the solvent, the product stream comprising at least 1-hexene; wherein n is a positive integer greater than or equal to 2; quenching the residual Ziegler-type catalyst in the product stream, and removing the residual ethylene and 1-butene from the product stream to form a higher LAO-enriched stream comprising $C_{6+}$ LAOs and the solvent; separating the 1-hexene from the higher LAO-enriched stream as an overhead stream from a first distillation column and a bottoms stream comprising $C_{8+}$ LAOs from the first distillation column; obtaining separated solvent as a side stream from the first distillation column or as a side stream from one of one or more downstream distillation columns; wherein at least one of the first distillation column or one or more of the one or more downstream distillation columns is a dividing wall column and the separated solvent is obtained from a dividing wall column; and returning the separated solvent to the reactor within the recycled solvent stream, the recycled solvent stream passing through one or more driers before returning to the reactor.

Embodiments A and B may have one or more of the following additional elements in any combination:

Element 1: wherein at least one of the first distillation column or one or more of the one or more downstream distillation columns is a dividing wall column.

Element 2: wherein the separated solvent is obtained from a dividing wall column.

Element 3: wherein the separated solvent is obtained as a side stream from the first distillation column and $C_{8+}$ LAOs are separated as a bottoms stream from the first distillation column.

Element 4: wherein the method further comprises: providing the bottoms stream comprising $C_{8+}$ LAOs to the first of the one or more downstream distillation columns; and separating individual LAO overhead streams from the one or more downstream distillation columns, each of the one or more downstream distillation columns providing a different individual LAO overhead stream.

Element 5: wherein the solvent is selected from the group consisting of methylcyclopentane, cyclohexane, isoheptane, 2,2-dimethylpentane, 2,2,4-trimethylpentane, methylcyclohexane, toluene, and any combination thereof.

Element 6: wherein the solvent comprises an aliphatic hydrocarbon solvent having a normal boiling point ranging from about 68° C. to about 116° C., and a solubility of water in the aliphatic hydrocarbon solvent is less than about 150 ppm.

Element 7: wherein a bottoms stream comprising $C_{8+}$ LAOs is provided to the first of the one or more downstream distillation columns; and wherein the separated solvent is obtained as a side stream from the first of the one or more downstream distillation columns, 1-octene is separated as an overhead stream from the first of the one or more downstream distillation columns, and $C_{10+}$ LAOs are separated as a bottoms stream from the first of the one or more downstream distillation columns.

Element 8: wherein the method further comprises separating individual LAO overhead streams from the one or more downstream distillation columns that are downstream from the first of the one or more downstream distillation columns, each of the one or more downstream distillation columns providing a different individual LAO overhead stream.

Element 9: wherein the solvent is selected from the group consisting of p-xylene, m-xylene, o-xylene, ethylbenzene, cyclooctane, 2-methyloctane, nonane, cumene, and any combination thereof.

Element 10: wherein the solvent comprises an aliphatic hydrocarbon solvent having a normal boiling point ranging from about 126° C. to about 167° C., and a solubility of water in the aliphatic hydrocarbon solvent is less than about 150 ppm at 25° C.

Element 11: wherein the one or more driers contain a drying agent selected from the group consisting of molecular sieves, an anhydrous salt, a reactive drying agent, and any combination thereof.

Element 12: wherein the separated solvent is obtained as a side stream from the first distillation column.

By way of non-limiting example, exemplary combinations include: The method of A in combination with elements 1 and 2; 1-3; 1 and 3; 1 and 5; 1 and 6; 1 and 7; 1 and 9; 1 and 10; 1 and 11; 2 and 3; 2 and 4; 2 and 5; 2 and 6; 2 and 7; 2 and 8; 2 and 9; 2 and 10; 2 and 11; 3 and 4; 3-5; 3 and 5; 3, 4 and 6; 3 and 6; 5 and 6; 7 and 8; 7-9; 7 and 9; 7 and 10; 7 and 11; 5 and 11; 6 and 11; 9 and 11; 10 and 11; 3, 4 and 11; 7, 8 and 11; 7-9 and 11; and 7, 10 and 11. By way of further non-limiting example, exemplary combinations also include the method of B in combination with elements 1 and 2; 1 and 5; 1 and 6; 1 and 7; 1 and 9; 1 and 10; 1 and 11; 2 and 3; 2 and 4; 2 and 5; 2 and 6; 2 and 7; 2 and 8; 2 and 9; 2 and 10; 2 and 11; 3 and 4; 3-5; 3 and 5; 3, 4 and 6; 3 and 6; 5 and 6; 5 and 11; 6 and 11; 9 and 11; 10 and 11; 3, 4 and 11; 7, 8 and 11; 7-9 and 11; 7, 10 and 11; land 12; 2 and 12; 5 and 12; 6 and 12; 4 and 12; 4, 5 and 12; 4, 6 and 12; 11 and 12; 7 and 8; 7-9; 7 and 9; 7 and 10; and 7 and 11.

This invention further relates to:

1. A method comprising:
   catalytically reacting ethylene in a reactor under oligomerization reaction conditions in the presence of a solvent and a Ziegler-type catalyst to form a product stream comprising one or more $C_{2n}H_{2n}$ linear alpha olefins (LAOS) and the solvent, the product stream comprising at least 1-hexene;
   wherein n is a positive integer greater than or equal to 2; and
   wherein the solvent is provided to the reactor from a recycled solvent stream having a water content such that a mole ratio of the Ziegler-type catalyst to water in the reactor is about 1000:1 or more (alternately, about 2000:1 or more, or about 3000:1 or more, or about 5000:1 or more, or about 10,000:1 or more);
   obtaining a higher LAO-enriched stream by removing residual ethylene and $C_4$ LAOs from the product stream, the higher LAO-enriched stream comprising $C_{6+}$ LAOs and the solvent;
   separating the 1-hexene from the higher LAO-enriched stream as an overhead stream from a first distillation column;
   obtaining separated solvent as a side stream from the first distillation column or as a side stream from a first of one or more downstream distillation columns; and
   returning the separated solvent to the reactor within the recycled solvent stream, the recycled solvent stream passing through one or more driers before returning to the reactor.

2. The method of paragraph 1, wherein at least one of the first distillation column or one or more of the one or more downstream distillation columns is a dividing wall column.

3. The method of paragraph 2, wherein the separated solvent is obtained from a dividing wall column.

4. The method of paragraph 2 or paragraph 3, wherein the separated solvent is obtained as a side stream from the first distillation column and $C_{8+}$ LAOs are separated as a bottoms stream from the first distillation column.

5. The method of paragraph 4, further comprising:
   providing the bottoms stream comprising $C_{8+}$ LAOs to the first of the one or more downstream distillation columns; and
   separating individual LAO overhead streams from the one or more downstream distillation columns, each of the one or more downstream distillation columns providing a different individual LAO overhead stream.
6. The method of any one of paragraphs 2-5, wherein the solvent is selected from the group consisting of methylcyclopentane, cyclohexane, isoheptane, 2,2-dimethylpentane, 2,2,4-trimethylpentane, methylcyclohexane, toluene, and any combination thereof.
7. The method of any one of paragraphs 2-5, wherein the solvent comprises an aliphatic hydrocarbon solvent having a normal boiling point ranging from about 68° C. to about 116° C., and a solubility of water in the aliphatic hydrocarbon solvent is less than about 150 ppm.
8. The method of paragraph 2 or paragraph 3, wherein a bottoms stream comprising $C_{8+}$ LAOs is provided to the first of the one or more downstream distillation columns; and
   wherein the separated solvent is obtained as a side stream from the first of the one or more downstream distillation columns, 1-octene is separated as an overhead stream from the first of the one or more downstream distillation columns, and $C_{10+}$ LAOs are separated as a bottoms stream from the first of the one or more downstream distillation columns.
9. The method of paragraph 8, further comprising:
   separating individual LAO overhead streams from the one or more downstream distillation columns that are downstream from the first of the one or more downstream distillation columns, each of the one or more downstream distillation columns providing a different individual LAO overhead stream.
10. The method of any one of paragraphs 2, 3, 8, or 9, wherein the solvent is selected from the group consisting of p-xylene, m-xylene, o-xylene, ethylbenzene, cyclooctane, 2-methyloctane, nonane, cumene, and any combination thereof.
11. The method of any one of paragraphs 2, 3, 8, or 9, wherein the solvent comprises an aliphatic hydrocarbon solvent having a normal boiling point ranging from about 126° C. to about 167° C., and a solubility of water in the aliphatic hydrocarbon solvent is less than about 150 ppm at 25° C.
12. The method of any preceding paragraph 1 to 11, wherein the one or more driers contain a drying agent selected from the group consisting of molecular sieves, an anhydrous salt, a reactive drying agent, and any combination thereof.
13. A method comprising:
    providing ethylene, a Ziegler-type catalyst, and a solvent to a reactor;
        wherein the solvent is provided to the reactor from a recycled solvent stream having a water content such that a mole ratio of the Ziegler-type catalyst to water in the reactor is about 1000:1 or more (alternately, about 2000:1 or more, or about 3000:1 or more, or about 5000:1 or more, or about 10,000:1 or more);
    catalytically reacting the ethylene in the reactor under oligomerization reaction conditions to form a product stream comprising one or more $C_{2n}H_{2n}$ linear alpha olefins (LAOs), residual ethylene, residual Ziegler-type catalyst, and the solvent, the product stream comprising at least 1-hexene;
        wherein n is a positive integer greater than or equal to 2;
    quenching the residual Ziegler-type catalyst in the product stream, and removing the residual ethylene and 1-butene from the product stream to form a higher LAO-enriched stream comprising $C_{6+}$ LAOs and the solvent;
    separating the 1-hexene from the higher LAO-enriched stream as an overhead stream from a first distillation column and a bottoms stream comprising $C_{8+}$ LAOs from the first distillation column;
    obtaining separated solvent as a side stream from the first distillation column or as a side stream from one of one or more downstream distillation columns;
        wherein at least one of the first distillation column or one or more of the one or more downstream distillation columns is a dividing wall column and the separated solvent is obtained from a dividing wall column; and
    returning the separated solvent to the reactor within the recycled solvent stream, the recycled solvent stream passing through one or more driers before returning to the reactor.
14. The method of paragraph 13, wherein the separated solvent is obtained as a side stream from the first distillation column.
15. The method of paragraph 13 or paragraph 14, further comprising:
    providing the bottoms stream comprising $C_{8+}$ LAOs to a first of the one or more downstream distillation columns; and
    separating individual LAO overhead streams from the one or more downstream distillation columns, each of the one or more downstream distillation columns providing a different individual LAO overhead stream.
16. The method of paragraph 14 or paragraph 15, wherein the solvent is selected from the group consisting of methylcyclopentane, cyclohexane, isoheptane, 2,2-dimethylpentane, 2,2,4-trimethylpentane, methylcyclohexane, toluene, and any combination thereof.
17. The method of paragraph 14 or paragraph 15, wherein the solvent comprises an aliphatic hydrocarbon solvent having a normal boiling point ranging from about 68° C. to about 116° C., and a solubility of water in the aliphatic hydrocarbon solvent is less than about 150 ppm at 25° C.
18. The method of paragraph 13, wherein the bottoms stream comprising $C_{8+}$ LAOs is provided to a first of the one or more downstream distillation columns; and
    wherein the separated solvent is obtained as a side stream from the first of the one or more downstream distillation columns, 1-octene is separated as an overhead stream from the first of the one or more downstream distillation columns, and $C_{10+}$ LAOs are separated as a bottoms stream from the first of the one or more downstream distillation columns.
19. The method of paragraph 18, further comprising:
    separating individual LAO overhead streams from the one or more downstream distillation columns that are downstream from the first of the one or more downstream distillation columns, each of the one or more downstream distillation columns providing a different individual LAO overhead stream.
20. The method of paragraph 18 or paragraph 19, wherein the solvent is selected from the group consisting of p-xylene, m-xylene, o-xylene, ethylbenzene, cyclooctane, 2-methyloctane, nonane, cumene, and any combination thereof 21. The method of paragraph 18 or paragraph 19, wherein the solvent comprises an aliphatic hydrocarbon solvent having a normal boiling point ranging from about 126° C. to about 167° C., and a solubility of water in the aliphatic hydrocarbon solvent is less than about 150 ppm.

22. The method of any one of paragraphs 13-21, wherein the one or more driers contain a drying agent selected from the group consisting of molecular sieves, an anhydrous salt, a reactive drying agent, and any combination thereof.

This invention further relates to:

1A. A method comprising:
catalytically reacting ethylene in a reactor under oligomerization reaction conditions in the presence of a solvent and a Ziegler-type catalyst to form a product stream comprising one or more $C_{2n}H_{2n}$ linear alpha olefins (LAOS) and the solvent, the product stream comprising at least 1-hexene;
wherein n is a positive integer greater than or equal to 2; and
wherein the solvent is provided to the reactor from a recycled solvent stream having a water content such that a mole ratio of the Ziegler-type catalyst to water in the reactor is about 1000:1 or more (alternately, about 2000:1 or more, or about 3000:1 or more, or about 5000:1 or more, or about 10,000:1 or more);
obtaining a higher LAO-enriched stream by removing residual ethylene and $C_4$ LAOs from the product stream, the higher LAO-enriched stream comprising $C_{6+}$ LAOs and the solvent;
separating the 1-hexene from the higher LAO-enriched stream as an overhead stream from a first distillation column;
obtaining separated solvent as a side stream from the first distillation column or as a side stream from a first of one or more downstream distillation columns; and
returning the separated solvent to the reactor within the recycled solvent stream, the recycled solvent stream passing through one or more driers before returning to the reactor.

2A. The method of paragraph 1A, wherein the separated solvent is obtained from a dividing wall column.

3A. The method of paragraph 1A, wherein at least one of the first distillation column or one or more of the one or more downstream distillation columns is a dividing wall column.

4A. The method of paragraph 1A, wherein the separated solvent is obtained as a side stream from the first distillation column and $C_{8+}$ LAOs are separated as a bottoms stream from the first distillation column.

5A. The method of paragraph 4A, further comprising:
providing the bottoms stream comprising $C_{8+}$ LAOs to the first of the one or more downstream distillation columns; and
separating individual LAO overhead streams from the one or more downstream distillation columns, each of the one or more downstream distillation columns providing a different individual LAO overhead stream.

6A. The method paragraph 1A, wherein the solvent is selected from the group consisting of methylcyclopentane, cyclohexane, isoheptane, 2,2,4-trimethylpentane, methylcyclohexane, toluene, and any combination thereof 7A. The method of paragraph 1A, wherein the solvent comprises an aliphatic hydrocarbon solvent having a normal boiling point ranging from about 68° C. to about 116° C., and a solubility of water in the aliphatic hydrocarbon solvent is less than about 150 ppm.

8A. The method of paragraph 1A, wherein a bottoms stream comprising $C_{8+}$ LAOs is provided to the first of the one or more downstream distillation columns; and
wherein the separated solvent is obtained as a side stream from the first of the one or more downstream distillation columns, 1-octene is separated as an overhead stream from the first of the one or more downstream distillation columns, and $C_{10+}$ LAOs are separated as a bottoms stream from the first of the one or more downstream distillation columns.

9A. The method of paragraph 8A, further comprising:
separating individual LAO overhead streams from the one or more downstream distillation columns that are downstream from the first of the one or more downstream distillation columns, each of the one or more downstream distillation columns providing a different individual LAO overhead stream.

10A. The method of paragraph 1A, wherein the solvent is selected from the group consisting of p-xylene, m-xylene, o-xylene, cyclooctane, 2-methyloctane, nonane, cumene, and any combination thereof.

11A. The method of paragraph 1A, wherein the solvent comprises an aliphatic hydrocarbon solvent having a normal boiling point ranging from about 126° C. to about 167° C., and a solubility of water in the aliphatic hydrocarbon solvent is less than about 150 ppm at 25° C.

12A. The method of paragraph 1A, wherein the one or more driers contain a drying agent selected from the group consisting of molecular sieves, an anhydrous salt, a reactive drying agent, and any combination thereof.

13A. A method comprising:
providing ethylene, a Ziegler-type catalyst, and a solvent to a reactor;
wherein the solvent is provided to the reactor from a recycled solvent stream having a water content such that a mole ratio of the Ziegler-type catalyst to water in the reactor is about 1000:1 or more (alternately, about 2000:1 or more, or about 3000:1 or more, or about 5000:1 or more, or about 10,000:1 or more);
catalytically reacting the ethylene in the reactor under oligomerization reaction conditions to form a product stream comprising one or more $C_{2n}H_{2n}$ linear alpha olefins (LAOs), residual ethylene, residual Ziegler-type catalyst, and the solvent, the product stream comprising at least 1-hexene;
wherein n is a positive integer greater than or equal to 2;
quenching the residual Ziegler-type catalyst in the product stream, and removing the residual ethylene and 1-butene from the product stream to form a higher LAO-enriched stream comprising $C_{6+}$ LAOs and the solvent;
separating the 1-hexene from the higher LAO-enriched stream as an overhead stream from a first distillation column and a bottoms stream comprising $C_{8+}$ LAOs from the first distillation column;
obtaining separated solvent as a side stream from the first distillation column or as a side stream from one of one or more downstream distillation columns;
wherein at least one of the first distillation column or one or more of the one or more downstream distillation columns is a dividing wall column and the separated solvent is obtained from a dividing wall column; and returning the separated solvent to the reactor within the recycled solvent stream, the recycled solvent stream passing through one or more driers before returning to the reactor.

14A. The method of paragraph 13A, wherein the separated solvent is obtained as a side stream from the first distillation column.

15A. The method of paragraph 14A, further comprising:
providing the bottoms stream comprising $C_{8+}$ LAOs to a first of the one or more downstream distillation columns; and
separating individual LAO overhead streams from the one or more downstream distillation columns, each of the one or more downstream distillation columns providing a different individual LAO overhead stream.

16A. The method of paragraph 14A, wherein the solvent is selected from the group consisting of methylcyclopentane, cyclohexane, isoheptane, 2,2,4-trimethylpentane, methylcyclohexane, toluene, and any combination thereof.

17A. The method of paragraph 14A, wherein the solvent comprises an aliphatic hydrocarbon solvent having a normal boiling point ranging from about 68° C. to about 116° C., and a solubility of water in the aliphatic hydrocarbon solvent is less than about 150 ppm at 25° C.

18A. The method of paragraph 13A, wherein the bottoms stream comprising $C_{8+}$ LAOs is provided to a first of the one or more downstream distillation columns; and
wherein the separated solvent is obtained as a side stream from the first of the one or more downstream distillation columns, 1-octene is separated as an overhead stream from the first of the one or more downstream distillation columns, and $C_{10+}$ LAOs are separated as a bottoms stream from the first of the one or more downstream distillation columns.

19A. The method of paragraph 18A, further comprising:
separating individual LAO overhead streams from the one or more downstream distillation columns that are downstream from the first of the one or more downstream distillation columns, each of the one or more downstream distillation columns providing a different individual LAO overhead stream.

20A. The method of paragraph 18A, wherein the solvent is selected from the group consisting of p-xylene, m-xylene, o-xylene, cyclooctane, 2-methyloctane, nonane, cumene, and any combination thereof.

21A. The method of paragraph 18A, wherein the solvent comprises an aliphatic hydrocarbon solvent having a normal boiling point ranging from about 126° C. to about 167° C., and a solubility of water in the aliphatic hydrocarbon solvent is less than about 150 ppm.

22A. The method of paragraph 13A, wherein the one or more driers contain a drying agent selected from the group consisting of molecular sieves, an anhydrous salt, a reactive drying agent, and any combination thereof.

To facilitate a better understanding of the embodiments described herein, the following examples of various representative embodiments are given. In no way should the following examples be read to limit, or to define, the scope of the present disclosure.

Examples

Example 1: A series of ethylene oligomerization reactions were conducted with a 1:1 ratio of ethylene to p-xylene solvent. The reaction was conducted in a liquid phase at 300 psig in a batch reactor using a Ziegler-type catalyst prepared from $ZrCl_4$, i-decyl acetate and diethylaluminum chloride. The Al:Zr molar ratio in the catalyst was 14:1. The catalyst productivity was 20,000 g LAOs/g Zr in formulated catalyst. Variable amounts of water were supplied in the ethylene to determine the effect of water upon the formation of polymers. Results are summarized in Table 1 below.

TABLE 1

| $Zr:H_2O$ Mole Ratio | Reaction Temperature (° C.) | Ethylene Conversion (%) | Results (% Polyethylene in LAO Product) |
|---|---|---|---|
| 25-50:1 | 180 | 50 | Reactor plugged in 7 hours |
| 20-40:1 | 180 | 50 | Reactor plugged in 2 hours |
| 2000-3000:1 | 170 | 60-70 | 0.03%-0.04% |
| 10,000:1 | 170 | 55 | 0.017% |

A ratio of $Zr:H_2O$ of 1000:1 corresponds to a water concentration in the solvent of about 50 ppb.

Example 2: Process Simulation #1. Process stream modeling was conducted with SMISCI Provision PROII™ software (version 9.3.2.) using both conventional distillation column arrangements configured to remove solvent as an overhead stream and distillation column arrangements configured to remove solvent as a side stream. A simulated LAO column feed having the composition shown in Table 2 was used for all process simulations. An aliphatic solvent having a boiling point between 68° C. and 116° C. was combined with the simulated LAO column feed.

TABLE 2

| LAO | Vol. % |
|---|---|
| 1-butene | 18.3 |
| 1-hexene | 18.1 |
| 1-octene | 16.0 |
| 1-decene | 12/4 |
| 1-dodecene | 9.5 |
| 1-tetradecene | 6.5 |
| 1-hexadecene | 5.2 |
| 1-octadecene | 4.0 |
| mixed $C_{20+}$ LAOs | 10.0 |

When solvent having a boiling in the range between 68° C. and 116° C. was mixed with LAOs having a higher boiling point than the solvent, 100% of the water was obtained with the solvent separated as an overhead stream in a conventional distillation column arrangement.

In contrast, when solvent having a boiling point in the range between 68° C. and 116° C. was mixed with $C_{6+}$ LAOs along with a nominal amount of water (10 kg/hr), only 0.13 kg/hr of water was fractionated with solvent in a side stream (FIG. 2). This represents a >99% reduction in water content within the solvent compared to that obtained when separating the solvent as an overhead stream. When a dividing wall column was used to separate the side stream (FIG. 3), no water was fractionated into the side stream.

Example 3: Process Simulation #2. The process simulation of Example 2 was repeated with a solvent having a boiling point between 126° C. and 167° C. When the solvent was mixed with LAOs having a higher boiling point than the solvent, 100% of the water was obtained with the solvent separated as an overhead stream in a conventional distillation column arrangement.

In contrast, when solvent having a boiling point in the range between 126° C. and 167° C. was mixed with $C_{8+}$ LAOs along with a nominal amount of water (10 kg/hr), only 0.13 kg/hr of water was fractionated with solvent in a side stream (FIG. 4). This represents a >99% reduction in water content within the solvent compared to that obtained when separating the solvent as an overhead stream. When a dividing wall column was used to separate the side stream (FIG. 5), no water was fractionated into the side stream.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A method comprising:
    catalytically reacting ethylene in a reactor under oligomerization reaction conditions in the presence of a solvent and a Ziegler-type catalyst to form a product stream comprising one or more $C_{2n}H_{2n}$ linear alpha olefins (LAOS) and the solvent, the product stream comprising at least 1-hexene;
    wherein n is a positive integer greater than or equal to 2; and
    wherein the solvent is provided to the reactor from a recycled solvent stream having a water content such that a mole ratio of the Ziegler-type catalyst to water in the reactor is about 1000:1 or more;
    obtaining a higher LAO-enriched stream by removing residual ethylene and $C_4$ LAOs from the product stream, the higher LAO-enriched stream comprising $C_{6+}$ LAOs and the solvent;
    separating the 1-hexene from the higher LAO-enriched stream as an overhead stream from a first distillation column;
    obtaining separated solvent as a side stream from the first distillation column or as a side stream from a first of one or more downstream distillation columns; and
    returning the separated solvent to the reactor within the recycled solvent stream, the recycled solvent stream passing through one or more driers before returning to the reactor.

2. The method of claim 1, wherein at least one of the first distillation column or one or more of the one or more downstream distillation columns is a dividing wall column.

3. The method of claim 2, wherein the separated solvent is obtained from a dividing wall column.

4. The method of claim 2, wherein the separated solvent is obtained as a side stream from the first distillation column and $C_{8+}$ LAOs are separated as a bottoms stream from the first distillation column.

5. The method of claim 4, further comprising:
    providing the bottoms stream comprising $C_{8+}$ LAOs to the first of the one or more downstream distillation columns; and
    separating individual LAO overhead streams from the one or more downstream distillation columns, each of the one or more downstream distillation columns providing a different individual LAO overhead stream.

6. The method of claim 2, wherein the solvent is selected from the group consisting of methylcyclopentane, cyclohexane, isoheptane, 2,2-dimethylpentane, 2,2,4-trimethylpentane, methylcyclohexane, toluene, and any combination thereof.

7. The method of claim 2, wherein the solvent comprises an aliphatic hydrocarbon solvent having a normal boiling point ranging from about 68° C. to about 116° C., and a solubility of water in the aliphatic hydrocarbon solvent is less than about 150 ppm.

8. The method of claim 2, wherein a bottoms stream comprising $C_{8+}$ LAOs is provided to the first of the one or more downstream distillation columns; and
wherein the separated solvent is obtained as a side stream from the first of the one or more downstream distillation columns, 1-octene is separated as an overhead stream from the first of the one or more downstream distillation columns, and $C_{10+}$ LAOs are separated as a bottoms stream from the first of the one or more downstream distillation columns.

9. The method of claim 8, further comprising:
separating individual LAO overhead streams from the one or more downstream distillation columns that are downstream from the first of the one or more downstream distillation columns, each of the one or more downstream distillation columns providing a different individual LAO overhead stream.

10. The method of claim 2, wherein the solvent is selected from the group consisting of p-xylene, m-xylene, o-xylene, ethylbenzene, cyclooctane, 2-methyloctane, nonane, cumene, and any combination thereof.

11. The method of claim 2, wherein the solvent comprises an aliphatic hydrocarbon solvent having a normal boiling point ranging from about 126° C. to about 167° C., and a solubility of water in the aliphatic hydrocarbon solvent is less than about 150 ppm at 25° C.

12. The method of claim 2, wherein the one or more driers contain a drying agent selected from the group consisting of molecular sieves, an anhydrous salt, a reactive drying agent, and any combination thereof.

13. A method comprising:
providing ethylene, a Ziegler-type catalyst, and a solvent to a reactor;
wherein the solvent is provided to the reactor from a recycled solvent stream having a water content such that a mole ratio of the Ziegler-type catalyst to water in the reactor is about 1000:1 or more;
catalytically reacting the ethylene in the reactor under oligomerization reaction conditions to form a product stream comprising one or more $C_{2n}H_{2n}$ linear alpha olefins (LAOs), residual ethylene, residual Ziegler-type catalyst, and the solvent, the product stream comprising at least 1-hexene;
wherein n is a positive integer greater than or equal to 2;
quenching the residual Ziegler-type catalyst in the product stream, and removing the residual ethylene and 1-butene from the product stream to form a higher LAO-enriched stream comprising $C_{6+}$ LAOs and the solvent;
separating the 1-hexene from the higher LAO-enriched stream as an overhead stream from a first distillation column and a bottoms stream comprising $C_{8+}$ LAOs from the first distillation column;
obtaining separated solvent as a side stream from the first distillation column or as a side stream from one of one or more downstream distillation columns;
wherein at least one of the first distillation column or one or more of the one or more downstream distillation columns is a dividing wall column and the separated solvent is obtained from a dividing wall column; and
returning the separated solvent to the reactor within the recycled solvent stream, the recycled solvent stream passing through one or more driers before returning to the reactor.

14. The method of claim 13, wherein the separated solvent is obtained as a side stream from the first distillation column.

15. The method of claim 13, further comprising:
providing the bottoms stream comprising $C_{8+}$ LAOs to a first of the one or more downstream distillation columns; and
separating individual LAO overhead streams from the one or more downstream distillation columns, each of the one or more downstream distillation columns providing a different individual LAO overhead stream.

16. The method of claim 14, wherein the solvent is selected from the group consisting of methylcyclopentane, cyclohexane, isoheptane, 2,2-dimethylpentane, 2,2,4-trimethylpentane, methylcyclohexane, toluene, and any combination thereof.

17. The method of claim 14, wherein the solvent comprises an aliphatic hydrocarbon solvent having a normal boiling point ranging from about 68° C. to about 116° C., and a solubility of water in the aliphatic hydrocarbon solvent is less than about 150 ppm at 25° C.

18. The method of claim 13, wherein the bottoms stream comprising $C_{8+}$ LAOs is provided to a first of the one or more downstream distillation columns; and
wherein the separated solvent is obtained as a side stream from the first of the one or more downstream distillation columns, 1-octene is separated as an overhead stream from the first of the one or more downstream distillation columns, and $C_{10+}$ LAOS are separated as a bottoms stream from the first of the one or more downstream distillation columns.

19. The method of claim 18, further comprising:
separating individual LAO overhead streams from the one or more downstream distillation columns that are downstream from the first of the one or more downstream distillation columns, each of the one or more downstream distillation columns providing a different individual LAO overhead stream.

20. The method of claim 18, wherein the solvent is selected from the group consisting of p-xylene, m-xylene, o-xylene, ethylbenzene, cyclooctane, 2-methyloctane, nonane, cumene, and any combination thereof.

21. The method of claim 18, wherein the solvent comprises an aliphatic hydrocarbon solvent having a normal boiling point ranging from about 126° C. to about 167° C., and a solubility of water in the aliphatic hydrocarbon solvent is less than about 150 ppm.

22. The method of claim 13, wherein the one or more driers contain a drying agent selected from the group consisting of molecular sieves, an anhydrous salt, a reactive drying agent, and any combination thereof.

* * * * *